(12) United States Patent
Kazerooni et al.

(10) Patent No.: US 9,308,112 B2
(45) Date of Patent: Apr. 12, 2016

(54) METHOD AND APPARATUS FOR HUMAN TRUNK SUPPORT DEVICE

(75) Inventors: Homayoon Kazerooni, Berkeley, CA (US); Kibeum Ryoo, Berkeley, CA (US); Han Woong Bae, Pittsburg, CA (US); Daniel Merala, San Carlos, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 336 days.

(21) Appl. No.: 13/807,456

(22) PCT Filed: Jun. 28, 2011

(86) PCT No.: PCT/US2011/042179
§ 371 (c)(1),
(2), (4) Date: Apr. 4, 2013

(87) PCT Pub. No.: WO2012/006087
PCT Pub. Date: Jan. 12, 2012

(65) Prior Publication Data
US 2013/0184626 A1     Jul. 18, 2013

Related U.S. Application Data

(60) Provisional application No. 61/359,115, filed on Jun. 28, 2010.

(51) Int. Cl.
*A61F 5/02* (2006.01)
*A61F 5/01* (2006.01)

(52) U.S. Cl.
CPC ........... *A61F 5/02* (2013.01); *A61F 2005/0188* (2013.01)

(58) Field of Classification Search
USPC .............. 602/5, 19, 16, 26–27; 601/5, 23, 24
See application file for complete search history.

(56) References Cited

U.S. PATENT DOCUMENTS

| | | | |
|---|---|---|---|
| 1,191,769 A * | 7/1916 | Curts | A61F 5/028 2/44 |
| 4,745,911 A * | 5/1988 | Bender | 482/139 |
| 4,829,989 A * | 5/1989 | Deamer | A61F 5/02 602/19 |
| 4,905,678 A * | 3/1990 | Cumins | A61F 5/0193 602/16 |
| 5,176,622 A * | 1/1993 | Anderson | A61F 5/02 482/124 |
| 5,207,635 A * | 5/1993 | Richards et al. | 602/19 |
| 8,177,733 B2 * | 5/2012 | Ashihara | A61F 5/0102 600/595 |
| 8,784,344 B2 * | 7/2014 | Takahashi | A61H 1/0244 601/35 |

(Continued)

*Primary Examiner* — Kim M Lewis
(74) *Attorney, Agent, or Firm* — Roberts Mlotkowski Safran & Cole, P.C.

(57) ABSTRACT

A trunk support device (100) is configurable to be worn by a person to reduce the muscle forces in the person's back during forward bending. The device (100), among other things, includes: a waist strap (102) which is configurable to be coupled to the person waist; a chest support (104) which is configurable to be coupled to the person's chest and capable of pushing against the person chest; and first and second torque generators (106) coupled to the chest support (104) and the waist strap (102) and capable of providing a resistance torque between them. In operation, when a person wearing the device (100) bends forward, at least one of the torque generators (106) imposes a torque between the chest support (104) and the waist strap (102), causing the chest support (104) to impose a force onto the person's chest backwardly and the waist strap (102) to impose a force onto the person's hip.

22 Claims, 13 Drawing Sheets

(56) References Cited

U.S. PATENT DOCUMENTS

| | | | |
|---|---|---|---|
| 2008/0161738 A1* | 7/2008 | Giesen | A61F 5/026 602/19 |
| 2009/0292369 A1* | 11/2009 | Kazerooni et al. | 623/27 |
| 2009/0312682 A1* | 12/2009 | Hirata | A61F 5/0193 602/23 |
| 2010/0004577 A1* | 1/2010 | Yasuhara | A63B 21/4011 602/23 |

* cited by examiner

US 9,308,112 B2

METHOD AND APPARATUS FOR HUMAN TRUNK SUPPORT DEVICE

CROSS-REFERENCE TO RELATED APPLICATIONS

The present invention claims the benefit of U.S. Provisional Patent Application Ser. No. 61/359,115 entitled "Method and Apparatus for Human Trunk Support Device" filed Jun. 28, 2010.

FIELD OF THE INVENTION

The present invention pertains to the art of support devices for the human spine and, more particularly, to a trunk support device configured to reduce the bending moment on a person's back during a forward bend.

DESCRIPTION OF THE PRIOR ART

In general, back support devices which are configured to assist a person in bending, lifting and/or standing upright are known in the art. Typical assisting devices are configured either with a lift assist device along the back of a wearer, or a lift assist device located along the front of a wearer. One example of a lift assist device located behind a wearer is depicted in U.S. Pat. No. 1,409,326, which utilizes an elongated spring member extending between a shoulder area of a wearer and a lower end, preferably a knee of a wearer. When the wearer bends over, the spring member is flexed and supports the bent over portion of the body. One example of a front located lift assist is depicted in U.S. Pat. No. 4,829,989, which utilizes a frame having a pair of arms each extending from a wearer's torso to the anterior portion of the wearer's upper leg, between the knee and hip. As the wearer bends, a spring begins to twist about a hub and provides a reactive force to support the upper torso of the wearer. Such prior art devices are seen to be fairly limited in functionality, and can include unnecessary bulky and burdensome frame elements. Additionally, such prior art devices limit the natural walking motion of a wearer. Therefore, there is seen to be a need in the art for an improved human trunk support device.

SUMMARY OF THE INVENTION

The present invention is directed to a trunk support device configurable to be worn by a person to reduce the muscle forces in the wearer's back during forward bending. The trunk support device includes a waist strap configured to couple to a wearer's waist and a chest support including a chest engagement piece configured to engage the wearer's chest. First and second torque generators connect to respective first and second hip portions of the waist strap and first and second opposing support bars of the chest support. In use, when the wearer bends forward, each of the first and second torque generators imposes a resistance torque between the chest support and the waist strap, causing the chest engagement piece to impose a force against the wearer's chest, and causing the waist strap to impose a force onto the wearer's hips. The torque generators can be passive or active components. The trunk support device may also include a controller configured to automatically adjust the amount of resistance torque imposed by the first and second torque generators based on signals from one or more sensors.

DETAILED DESCRIPTION OF PREFERRED EMBODIMENTS

Figure 1:
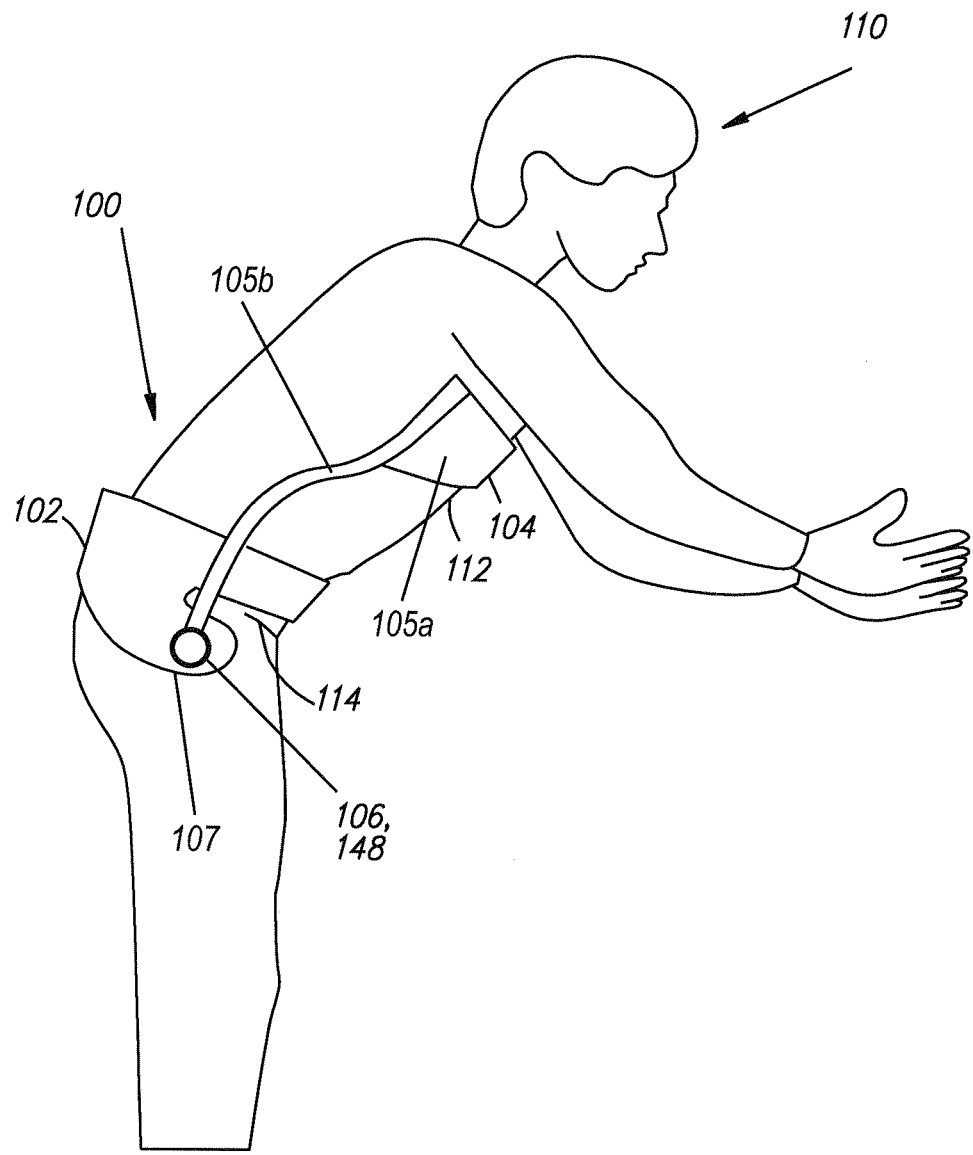
FIG. 1 is depicts a trunk support device of the present invention on a forward leaning wearer.

FIG. 1 illustrates a trunk support device 100 of the present invention. Trunk support device 100 is configured to be worn by a person 110 to reduce the bending moment in the person's back during forward bending as shown in FIG. 1. The reduction of this bending moment, in return, reduces the spine compression force and the spine muscle tensile force (e.g., the force in erector spinae). The reduction of the spine compression force and the spine muscle tensile force leads to less risk of back injuries. Trunk support device 100 includes: a waist strap 102 which is configured to be coupled to a person's waist and rest on the person's hips 114; a chest support 104 which is configured to be coupled to or engage the person chest 112; and first and second opposing torque generators, one of which is depicted at 106. In general, chest support 104 includes a chest engagement piece 105a adapted to engage the wearer's chest 112, and first and second opposing support bars, one of which is depicted at 105b, connected to opposing side portions of chest engagement piece 105a. First and second opposing support bars 105b connect chest support 104 to first and second opposing hip portions 107 of waist strap 102 through first and second torque generators 106.

Torque generators 106 may be passive or active, and are each configured to provide a resistance torque between chest support 104 and waist strap 102. By resistance torque it should be understood to mean that torque generators 106 resist the relative movement between chest support 104 and waist strap 102. The connection of chest support 104 to waist strap 102 via torque generators 106 eliminates the need for additional straps or supports which would add to the complexity of the device and which may interfere with natural movement of the wearer. Additionally, providing opposing torque generators 106 distributes forces to each hip area 114 of a wearer and enables a user to sit with relative comfort compared with prior art devices which locate a torque device behind a user.

Figure 5:
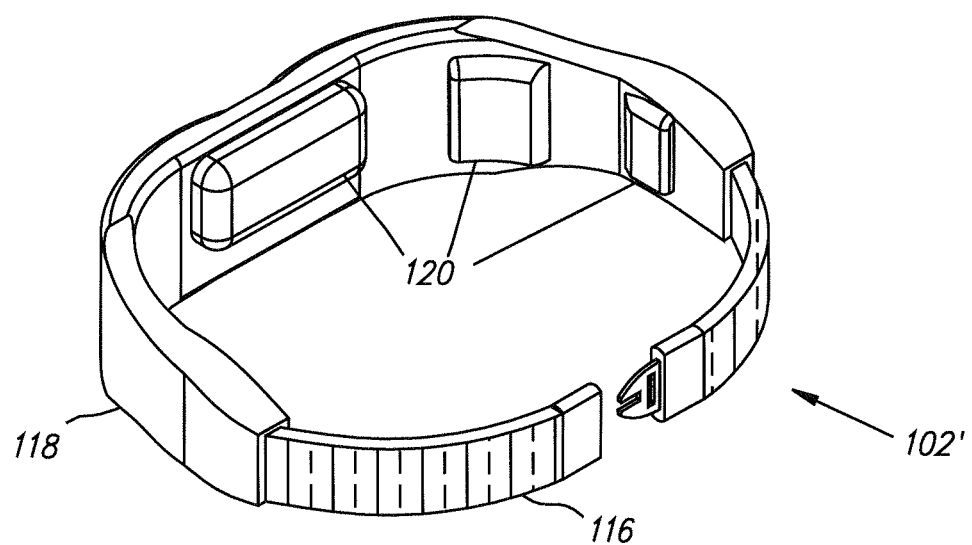
FIG. 5 depicts an alternative embodiment of a waist strap for use with the present invention.

Waist strap 102 may be constructed from various materials. FIG. 5 shows a waist strap 102' in accordance with one preferred embodiment of the present invention where a posterior portion 118 is constructed from hard or stiff materials to resist reaction torque induced by the torque applied by the torque generators 106. An anterior portion 116 is constructed from one or more soft or pliant materials to be gentle with the wearer's body especially on the hip and abdominal area. Examples of hard materials include, without limitation, aluminum, metals, plastic, and carbon fiber. Examples of soft materials include, without limitation, leather, rubber, cloth, fabric, plastic, and fibers. Preferably, waist strap 102' also includes soft padding 120 to create comfort for the user.

Figure 6:
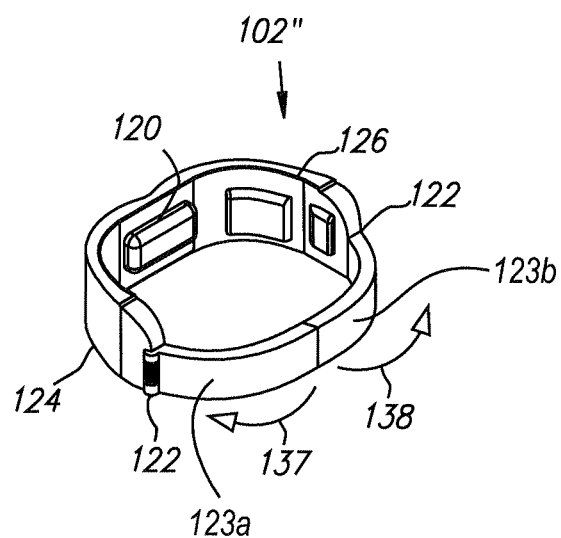
FIG. 6 depicts another alternative embodiment of a waist strap for use with the present invention.

FIG. 6 shows a waist strap 102" in accordance with another embodiment of the present invention wherein an outer part 124 is constructed from hard or stiff materials. An inner part 126 is constructed from softer materials such as foam, rubber, cotton, or fabric for the user's comfort. Inner part 126 may also include soft padding 120 to create more comfort for the user. Additionally, two hinges 122 are used to open first and second hinged arms 123a and 123b of waist strap 102" along arrows 137 and 138. This allows convenient coupling between a wearer of trunk support device 100 or person 110, and waist strap 102".

Figure 7:
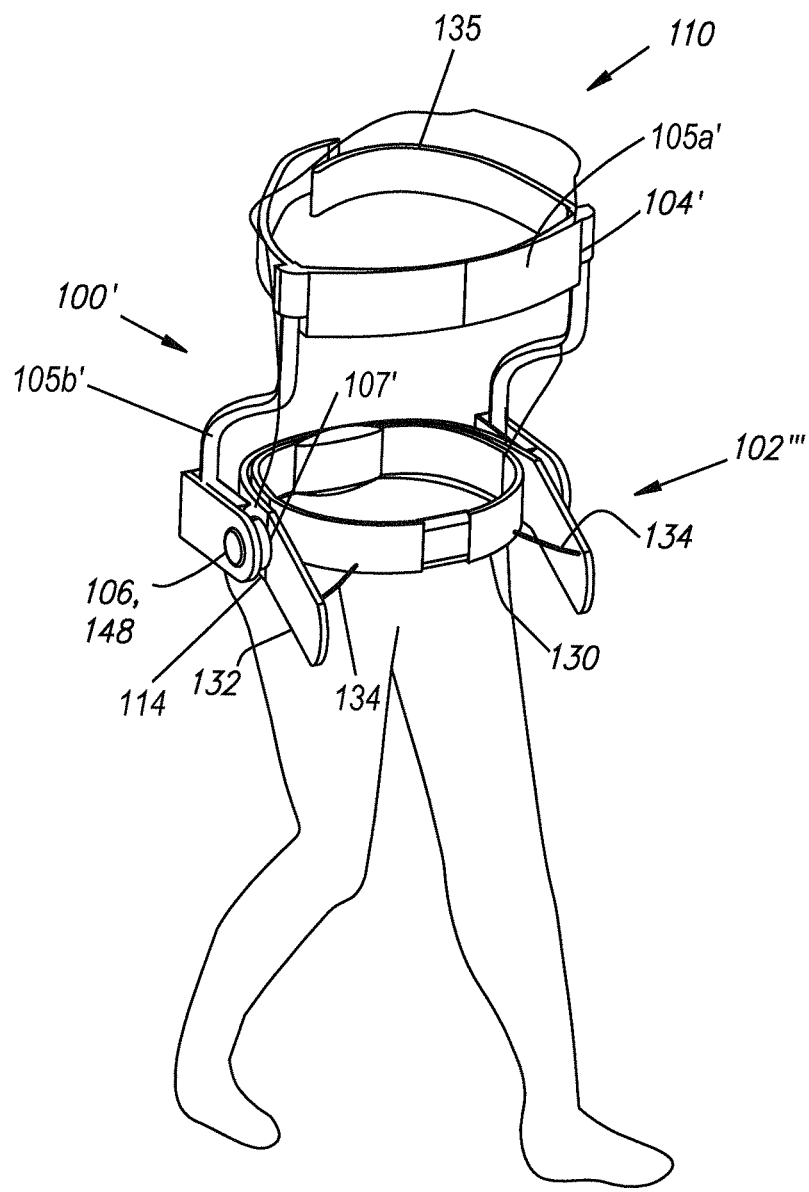
FIG. 7 depicts an alternative embodiment of the trunk support device of the present invention.
Figure 8:
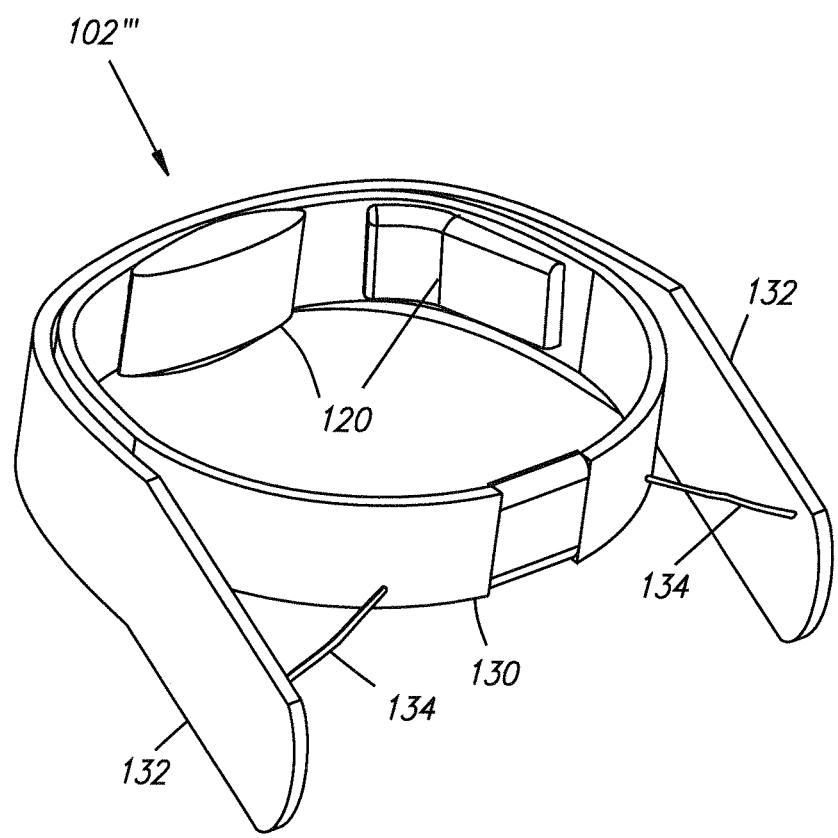
FIG. 8 depicts the waist strap of FIG. 7.

FIG. 7 shows yet another waist strap 102''', which includes two parts: a waist belt 130 and a waist bracket 132 with first and second hip portions 107'. FIG. 8 shows the close-up view of waist strap 102''' (where person 110, torque generators 106 and chest support 104 have been removed for clarity). The waist bracket 132 is constructed from hard materials to resist the reaction torque of torque generators 106. Waist belt 130 is constructed from softer materials to be gentle with the person's body especially on the hip and abdominal areas. Waist belt 130 and waist bracket 132 are coupled to each other generally at a back area of person 114. Examples of hard materials that are used in construction of waist bracket 132 include, without limitation, aluminum, metals, plastic, and carbon fiber. Examples of soft materials that are used in construction of waist belt 130 include, without limitation, leather, rubber, cloth, fabric, plastic, and fibers. First and second lines 134 connect waist belt 130 to waist bracket 132. Lines 134 transfer forces from waist bracket 132 to waist belt 130 and consequently onto the person's hip area 114. Lines 134 can be any type of rope, wire, ribbon or other material capable of providing a tensile force. FIG. 7 also depicts an alternative embodiment of chest support 104', which includes a chest strap 135 configured to wrap around the upper body portion of a wearer to secure chest support 104' to the wearer. Chest strap 135 is connected to each of first and second opposing support bars 105b', and includes a chest engagement portion 105a' that pushes against chest 112 of the wearer when the wearer bends forward.

Figure 9:
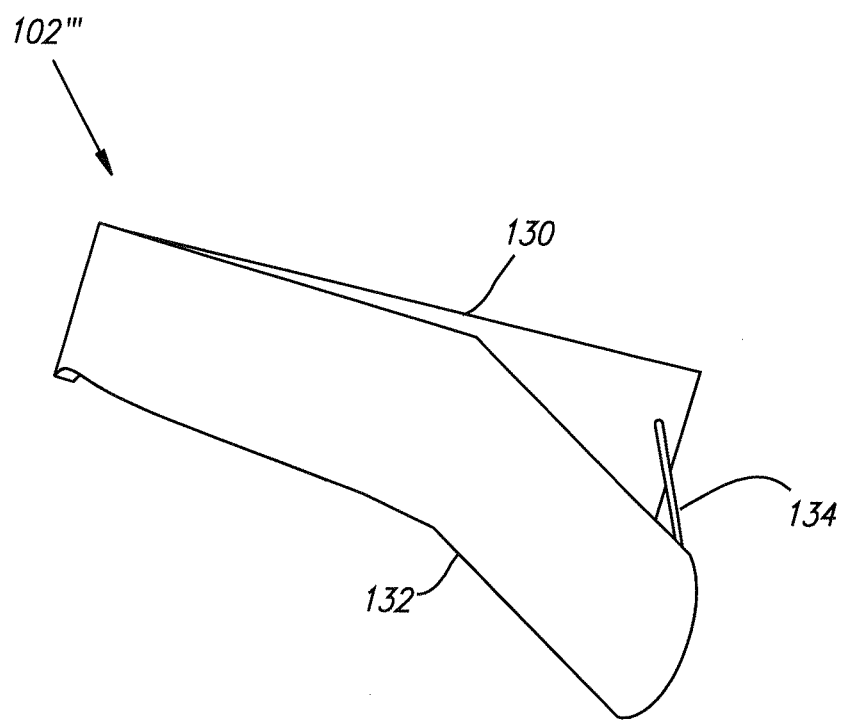
FIG. 9 depicts a side view of the waist strap of FIG. 8.
Figure 10:
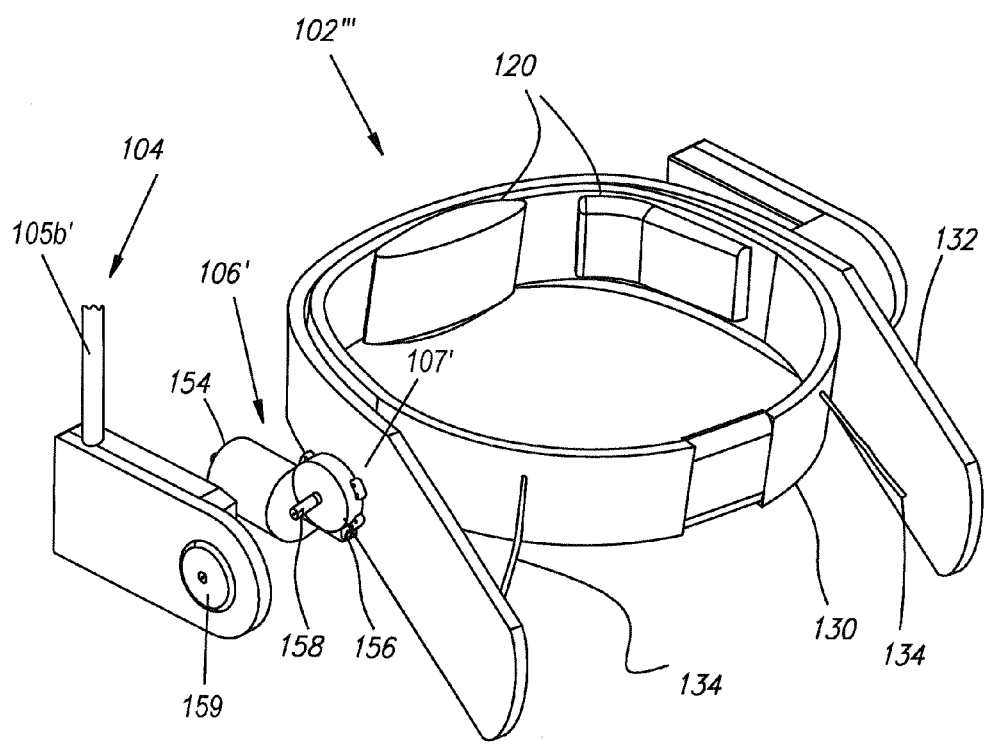
FIG. 10 depicts one embodiment of the torque generator of the present invention.

FIG. 9 shows a side view of waist strap 102'''. As can be seen from FIG. 9, lines 134 provide a tensile force to ensure waist belt 130 is imposing a force onto the person's hip 114. FIG. 10 shows waist strap 102''' of FIG. 8 including an exploded view of an active torque generator 106'. Examples of active torque generators 106' which can be utilized with the present invention include, without limitation, hydraulic motors, pneumatic motors, and electric motors including, without limitation, alternating current (AC) motors, brush-type direct current (DC) motors, brushless DC motors, electronically commutated motors (ECMs), stepping motors, and combinations thereof. In the example shown in FIG. 10, at least one of torque generators 106' includes an electric motor 154 and a transmission 156. In this embodiment, electric motor 154 and transmission 156 are mounted on waist bracket 132 and a transmission output shaft 158 drives the movement of chest bracket 104 through its connection with a mounting element 159. Thus, it should be understood that the resistance supplied by first and second torque generators 106' between chest support 104 and waist strap 102''' imposes a force $F_C$ onto the person's chest 112 in the manner depicted in FIG. 2. This torque also causes waist strap 102''' to impose a force $F_H$ onto the person's hip 114.

Figure 2:
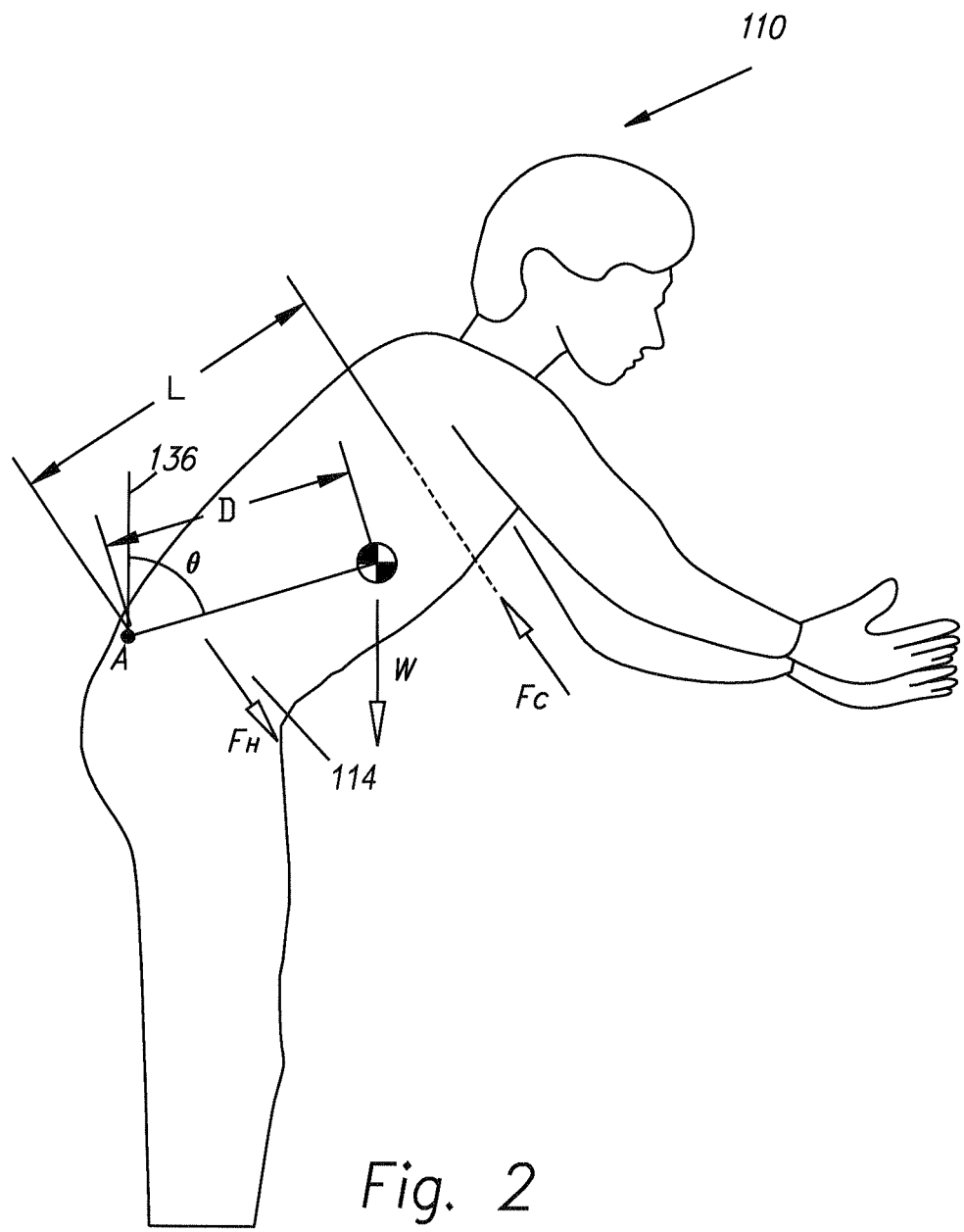
FIG. 2 is depicts forces imparted on the wearer of FIG. 1, with the trunk support device removed for clarity.

The forces imposed on a wearer and trunk support device 100 will now be discussed in more detail with reference to FIGS. 2 and 3. In operation, when person 110 wearing trunk support device 100 bends in a forward direction, at least one, and preferably both, of torque generators 106 produce a resistance torque between chest support 104 and waist strap 102. FIG. 2 depicts person 110 and the forces that are imposed on person 110. Force $F_C$ creates a moment about point A on the person's back (generally at the L5S1 joint). The upper body weight W also creates a moment about point A. The moment M about point A, when trunk support device 100 is worn, is expressed by equation 1.

$$M = WD \sin(\theta) - F_C L \quad (1)$$

Where:
M: The moment imposed on the person at L5/S1 joint by $F_C$ and the upper body weight, W.
W: Upper body weight including the weight of torso, head, arms and any object held by the arms or situated on the person's back.
D: The distance from upper body center of mass to point A.
θ: The angle shown in FIG. 2 which depicts how much a wearer has bent from a vertical line. Specifically, this angle is between a line drawn from an upper body center of mass and a vertical line.
$F_C$: The force from chest support 104 onto the person's chest 112.
$F_H$: The force from waist strap 102 onto the person's hip 114.
L: The normal distance from $F_C$ to point A.

Importantly, $F_H$ is imposed onto the person's hip 114 and does not produce any substantial moment at the L5/S1 joint. If no trunk support device 100 was worn by person 110, then the moment imposed on the person at L5/S1 joint would have been just due to the upper body weight, W. It can be observed from equation (1) that the moment at point A is reduced to M=WD Sin(θ)−$F_C$L due to force $F_C$, which is created by the chest support 104 onto the person's chest 112. One can set or adjust device 100 such that $F_C$ is equal to (or approximately equal to) WD SIN(θ). This will cause M to be zero or a very small quantity depending on how precisely the device is set or adjusted.

Figure 3:
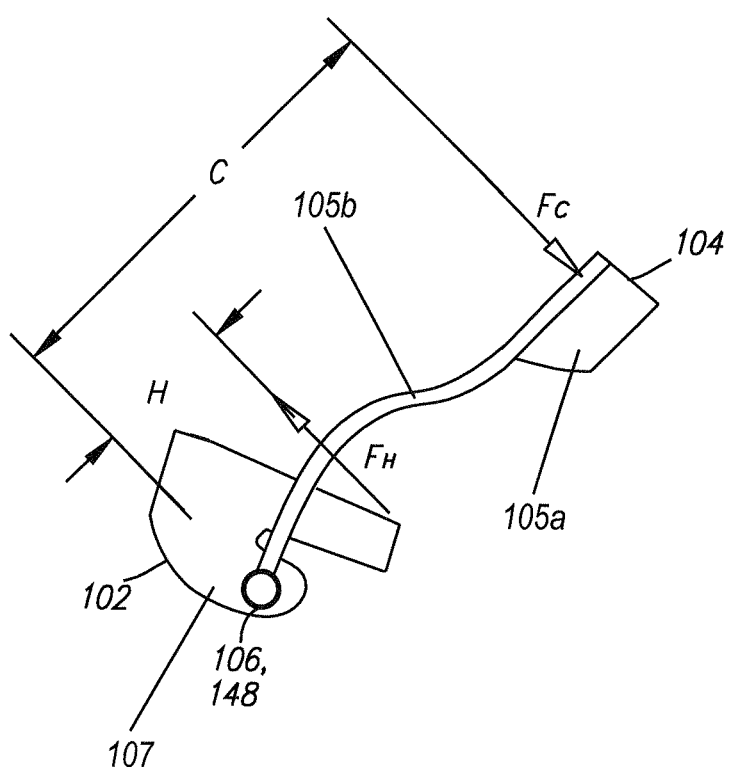
FIG. 3 depicts forces imparted on the trunk support device of FIG. 1.

The reaction force of $F_H$ and $F_C$ are shown in FIG. 3. Considering FIG. 3, at static equilibrium, equation (2) is true.

$$F_H H = F_C C \quad (2)$$

Where H and C represent the normal distance from $F_H$ and $F_C$ to a respective torque generator 106.

$$\text{Or: } F_H = \frac{C}{H} F_C \quad (3)$$

It can be seen from equation (3) that $F_H$ is usually larger than $F_C$. Substituting for $F_C$ from equation (1) into equation (3) results in equation (4) for the force imposed on the person's hip 114 from waist strap 102.

$$F_H = \frac{C}{HL}[WD\sin(\theta) - M] \quad (4)$$

It can be seen from equation (4) that, if torque generators 106 cause the moment at L5S1 joint to become zero (i.e., M=0), then $F_H$ (the force on hip areas 114) increases as person 110 bends (i.e., as θ increases). It can also be seen from equation (4) that, if torque generators 106 do not cause the torque at L5S1 joint to become zero (i.e., an ineffective support device is utilized or the device is not worn), then $F_H$ will always be zero. This means the present invention reduces the moment at point A but, in return, it produces a force on the person's hip areas 114.

Figure 4:
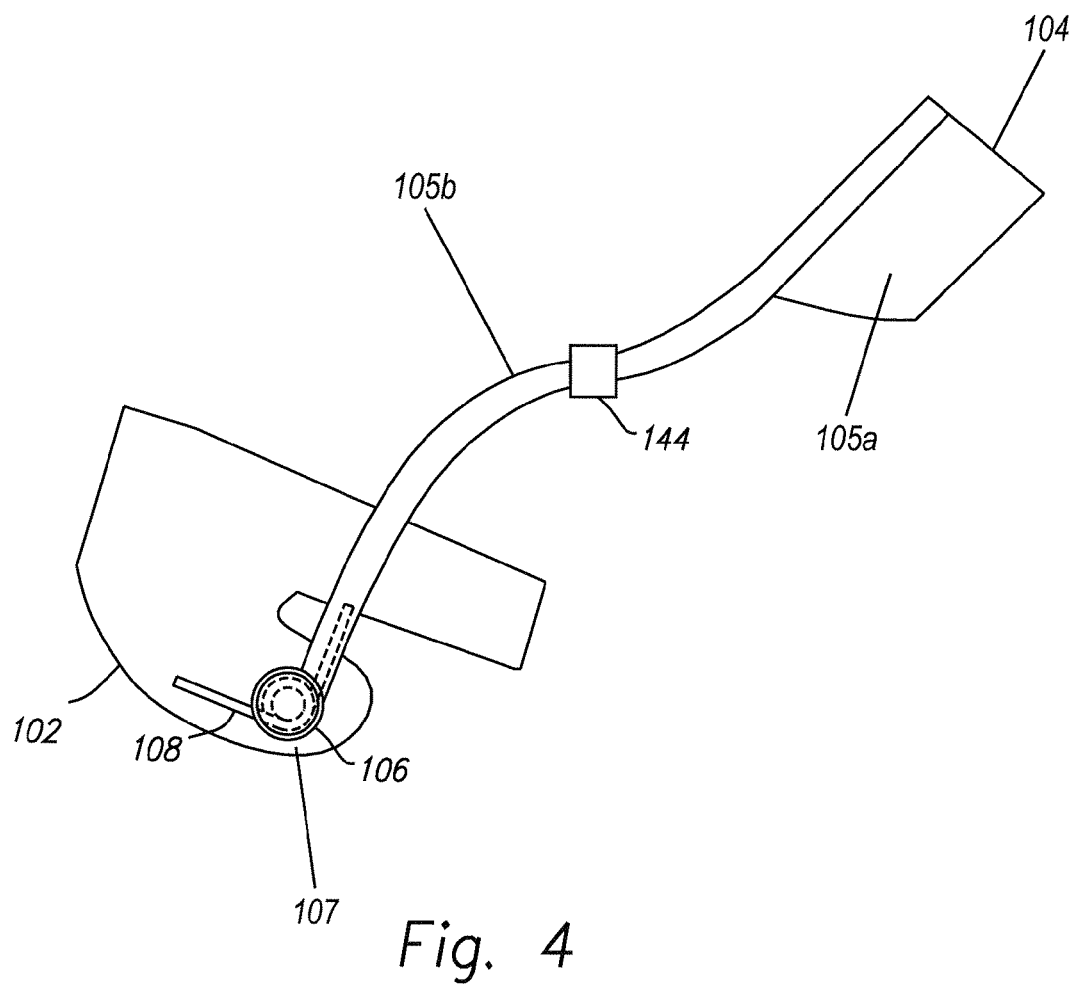
FIG. 4 is a trunk support device of the present invention including a spring.

One or both of torque generators 106 may be in the form of passive resilient torque generators that create torque when their shape changes. Examples of passive resilient torque generators include, without limitation, springs such as coil springs, leaf springs, tensile springs, air springs, gas springs, and compression springs. FIG. 4 shows an embodiment where a torsion spring 108 is used as the torque generator. As person 110 bends, the torque in torsion spring 108 increases to produce force $F_C$, as depicted in FIG. 3. The moment M associated with force $F_C$ cancels the moment associated with the upper body weight as prescribed by equation (1).

Figure 11:
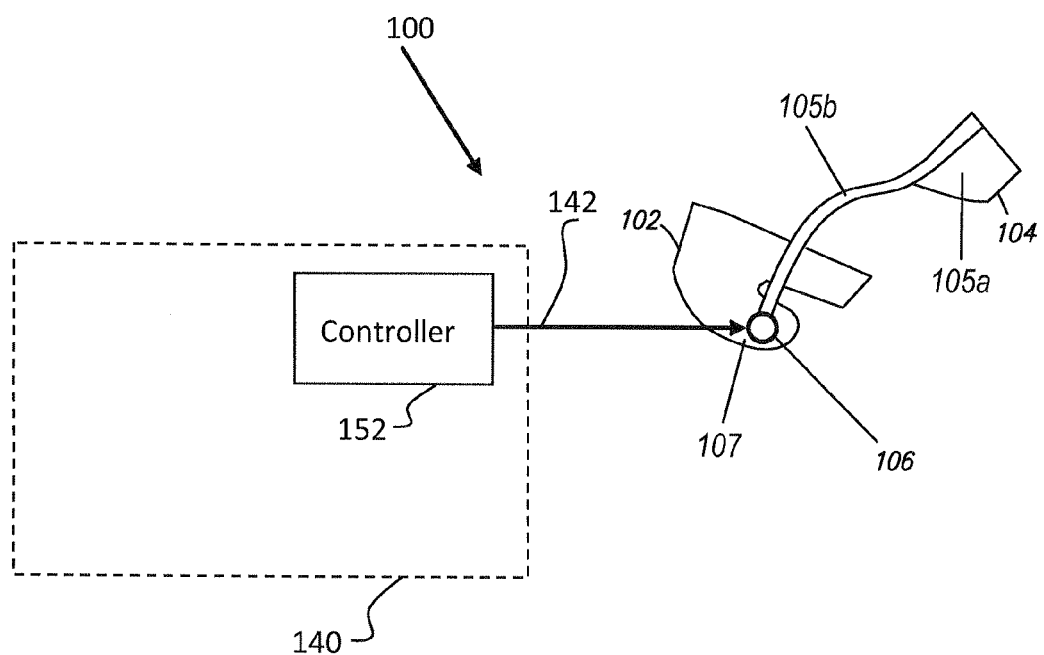
FIG. 11 is a partial schematic view of a control system for use with the present invention.
Figure 12:
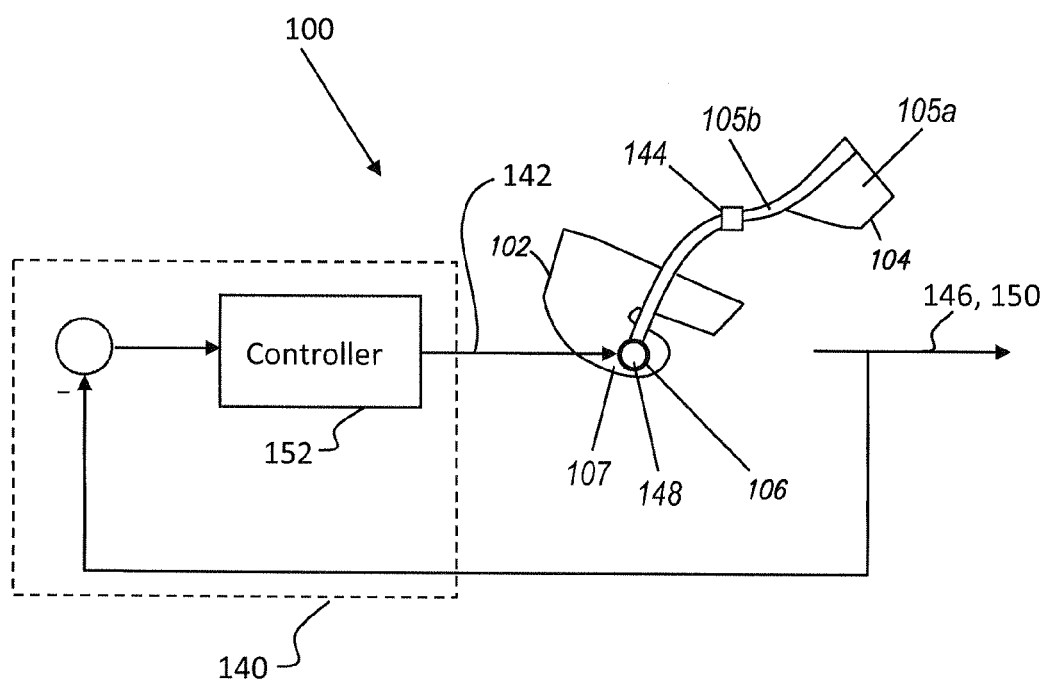
FIG. 12 is a partial schematic view of a control system for use with the present invention.

The manner in which the resistance torque can be automatically adjusted in accordance with the present invention will now be discussed with reference to FIGS. 11-13. In a preferred embodiment, trunk support device 100 includes a signal processor 140 configured to produce a control signal 142 for torque generators 106, wherein control signal 142 drives torque generators 106. Signal processor 140 incorporates a controller 152 which produces control signal 142 for torque generators 106 as a function of a set of input signals that signal processor 140 receives. Examples of input signals that signal processor 140 receives include, without limitation, a signal representing an angle of waist strap 102 with respect to chest support 104, a signal representing the velocity of chest support 104 with respect to waist strap 102, a signal representing the acceleration of chest support 104 with respect to waist strap 102, a signal representing the absolute angle of chest support 104, a signal representing the absolute velocity of chest support 104, a signal representing the absolute acceleration of chest support 104, a signal representing at least one torque generator's 106 movement, a signal representing at least one torque generator's 106 speed, a signal representing at least one torque generator's 106 acceleration, a signal representing at least one torque generator's 106 torque, a signal representing at least one torque generator's 106 force, a signal representing the person's movement, a signal representing the person's bending angle, a signal representing the person's bending velocity, a signal representing the person's bending acceleration, a signal representing the contact force between person 110 and chest support 104, and combinations thereof.

Various sensors can be utilized to provide controller 152 with the necessary signal information. In the preferred embodiment depicted in FIG. 12, trunk support device 100 includes a first sensor 144 generating a first signal 146 representing an output from first sensor 144. In a first example, first sensor 144 is an absolute angle sensor and first signal 146 is an absolute angle signal representing the angle that person 110 or chest support 104 has bent forward relative to vertical line 136 (shown in FIG. 2). However, it should be understood that first sensor 144 could be a velocity sensor, an accelerometer or other type of movement sensor. Trunk support device 100 can also include a second sensor 148 (shown in FIG. 12) generating a second signal 150 representing an output from second sensor 148. In a first example, second sensor 148 is an angle sensor and second signal 150 is an angle signal representing the angle of chest support 104 with respect to waist strap 102. In general, second sensor 148 is either included in at least one of torque generators 106 (as depicted in FIGS. 1, 3 and 7) or installed on the same location on waist strap 102 or chest support 104 that the at least one torque generator 106 is installed. However, it should also be understood that second sensor 148 can be a torque generator movement sensor, a torque generator speed sensor, a torque generator accelerometer, a torque generator force sensor, or any type of standard movement sensor. In operation, as shown in FIG. 12, signal processor 140 produces control signal 142 for torque generators 106 as a function of first signal 146 and/or second signal 150. That is, controller 152 utilizes first and second signals 146 and 150 as a feedback signal to generate control signal 142. The type of controller utilized dictates the magnitude of the resistance torque. One can find a variety of algorithms for controller 152 to perform the indicated task. In general, controllers with large gains lead to large resistance torques, while controllers with small gains result in smaller resistance torque.

Figure 13:
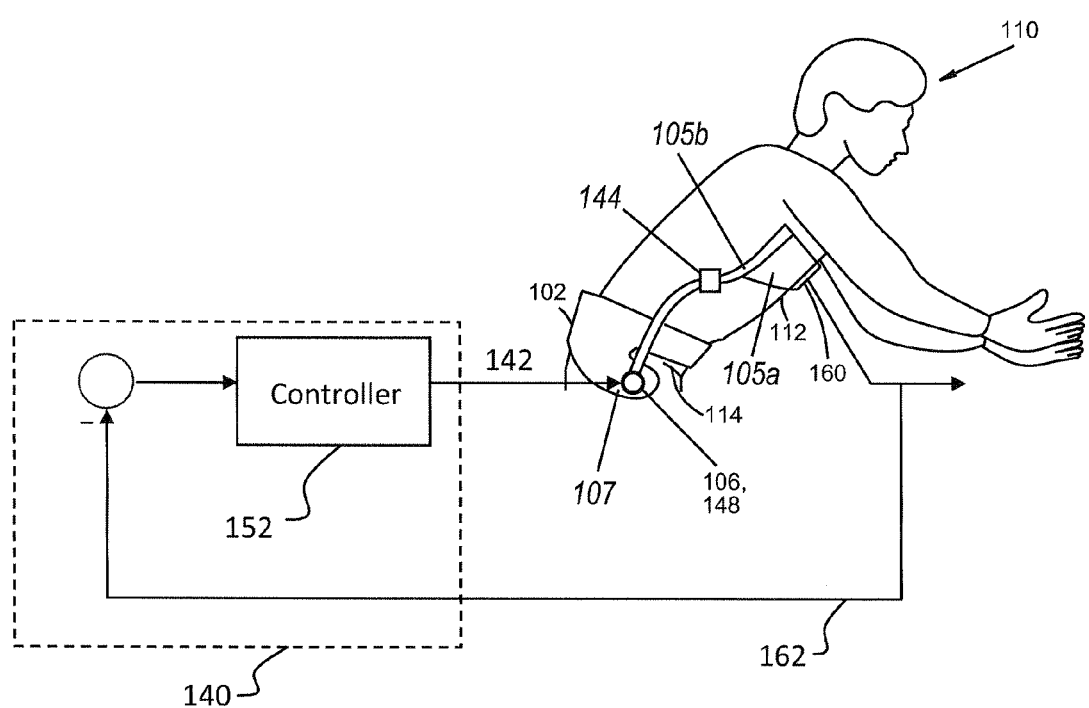
FIG. 13 is a partial schematic view of a control system for use with the present invention.

As shown in FIG. 13, trunk support device 100 may also include a force or pressure sensor 160 generating a force or pressure signal 162 representing the force or pressure between person 110 and chest support 104 ($F_C$). In operation, signal processor 140 produces control signal 142 for torque generators 106 as a function of force or pressure signal 162. That is, controller 152 utilizes force or pressure signal 162 as a feedback signal to generate control signal 142.

From the discussion above, it should be understood that controller 152 can be programmed and configured to activate torque generators 106 in a variety of ways based on signals 146, 150 and/or 162 from sensors 144, 148 and/or 160. In some embodiments of the invention, the resistance torque is a function of how much person 110 is bending forward. For example, in some embodiments of the invention, the resistance torque increases as person 110 bends forward. In some embodiments of the invention, the resistance torque is a function of the angle θ between person 110 and a vertical line 136 passing through a portion of a person, such as point A shown in FIG. 2. In some embodiments of the invention, the resistance torque increases linearly as the angle between person 110 and vertical line 136 (shown in FIG. 2) increases. In some embodiments of the invention, the resistance torque is a function of how much chest support 104 moves toward waist strap 102. In some embodiments of the invention, the resistance torque is a function of the angle between chest support 104 and vertical line 136. In some embodiments of the invention, the resistance torque increases linearly as the angle θ between chest support 104 and vertical line 136 increases. Finally, in some embodiments of the invention, the controller is configured to adjust the resistance torque imposed by the first and second torque generators to be generally constant for at least one segment of a bending movement of a wearer.

Although described with reference to preferred embodiments of the invention, it should be readily understood that various changes and/or modifications can be made to the invention without departing from the spirit thereof. For instance, the various chest supports, waist supports, torque generators and sensors can be combined in various ways to form different overall embodiments of the present invention. In general, the invention is only intended to be limited by the scope of the following claims.

The invention claimed is:

1. A trunk support device configurable to be worn by a person to reduce muscle forces in a wearer's back during forward bending, the trunk support device comprising:
   a waist strap configured to couple to a wearer's waist and including first and second hip portions;
   a chest support including a chest engagement piece configured to engage a wearer's chest and first and second opposing support bars connected to opposing side portions of the chest engagement piece; and first and second torque generators, each of the first and second torque generators connected to a respective one of the first and second hip portions of the waist strap and a respective one of the first and second opposing support bars of the chest support, wherein, when a wearer bends forward, said first and second torque generators each impose a resistance torque between said chest support and said waist strap, cause said chest engagement piece to impose a force against a wearer's chest, and cause said waist strap to impose a force onto a wearer's hips.

2. The trunk support device of claim 1, wherein at least one of said first and second torque generators is a passive resilient component.

3. A trunk support device of claim 1, wherein at least one of the first and second torque generators includes active components selected from the group consisting of hydraulic motors, hydraulic actuators, pneumatic motors, pneumatic actuators, electric motors and combinations thereof.

4. The trunk support device of claim 1, further comprising a controller configured to automatically adjust an amount of resistance torque imposed by said first and second torque generators.

5. The trunk support device of claim 1, further comprising:
at least one sensor; and
a signal processor configured to produce a control signal for the first and second torque generators based on at least one input signal from the at least one sensor.

6. The trunk support device of claim 5, wherein the at least one sensor is selected from the group consisting of a velocity sensor, an accelerometer, a force sensor, a pressure sensor, an angle sensor, a torque generator movement sensor, a torque generator speed sensor, a torque generator force sensor, or a combination thereof.

7. The trunk support device of claim 5, wherein said at least one input signal is selected from the group consisting of a signal representing an angle of the chest support with respect to the waist strap, a signal representing a velocity of the chest support with respect to the waist strap, a signal representing an acceleration of the chest support with respect to the waist strap, a signal representing an absolute angle of the chest support, a signal representing an absolute velocity of the chest support, a signal representing an absolute acceleration of the chest support, a signal representing movement of the torque generator, a signal representing a speed of the torque generator, a signal representing acceleration of the torque generator, a signal representing torque of the torque generator, a signal representing a force of the torque generator, a signal representing a wearer's movement, a signal representing a wearer's bending angle, a signal representing a wearer's bending velocity, a signal representing a wearer's bending acceleration, a signal representing a contact force between a wearer and the chest strap, and combinations thereof.

8. The trunk support device of claim 7, wherein the resistance torque imposed by the at least one of the first and second torque generators is a function of how much a wearer is bending forward.

9. The trunk support device of claim 1, wherein the resistance torque imposed by at least one of the first and second torque generators increases automatically as a wearer bends forward.

10. The trunk support device of claim 1, wherein the resistance torque imposed by at least one of the first and second torque generators increases linearly as the angle between a wearer and a vertical line increases.

11. The trunk support device of claim 1, wherein the resistance torque imposed by at least one of the first and second torque generators increases linearly as an angle between said chest support and a vertical line increases.

12. The trunk support device of claim 1, wherein the resistance torque imposed by at least one of the first and second torque generators is generally constant for at least one segment of a bending movement of a wearer.

13. The trunk support device of claim 1, wherein said waist strap is constructed, at least in part, by a stiff material resistant to movement induced by the resistance torque between said chest support and said waist strap.

14. The trunk support device of claim 13, wherein a first portion of said waist strap is constructed from a stiff material to resist movement induced by the resistance torque between said chest support and said waist strap, and a second portion of said waist strap adapted to be in contact with a wearer's body is constructed from a soft material.

15. The trunk support device of claim 14, wherein said waist strap further includes first and second hinged arms adapted to removably connect to one another and enable coupling of the waist strap to a wearer.

16. The trunk support device of claim 13, wherein said waist strap further includes:
a waist belt adapted to couple the waist strap to a wearer, a waist bracket coupled to the first and second torque generators and a line connecting the waist belt to the waist bracket, wherein said waist belt and said waist bracket are coupled to each other generally at the back area of a wearer and said line transfers forces from the waist bracket to the waist belt and consequently onto a wearer's hip region.

17. A method of reducing muscle forces in a wearer's back during forward bending using a trunk support device, the trunk support device including a waist strap, a chest support, and first and second torque generators connected to respective first and second opposing hip portions of the waist strap and first and second opposing support bars of the chest support, the method comprising:
imposing a resistance torque between said chest support and said waist strap via said first and second torque generators when the wearer bends forward to cause a chest engagement piece of the chest support to impose a force against the wearer's chest, and cause said waist strap to impose a force onto the wearer's hips.

18. The method of claim 17, wherein the first and second torque generators are active components selected from the group consisting of hydraulic motors, hydraulic actuators, pneumatic motors, pneumatic actuators, electric motors and combinations thereof.

19. The method of claim 18, further comprising the step of:
adjusting the amount of resistance torque imposed by said first and second torque generators.

20. The method of claim 19, wherein the step of adjusting the amount of resistance torque is performed utilizing a controller based on at least one input signal received from at least one sensor of the trunk support device.

21. The method of claim 20, wherein the at least one sensor is selected from the group consisting of a velocity sensor, an accelerometer, a force sensor, a pressure sensor, an angle sensor, a torque generator movement sensor, a torque generator speed sensor, a torque generator force sensor, or a combination thereof.

22. The method of claim 20, wherein said at least one input signal is selected from the group consisting of a signal representing an angle of the chest support with respect to the waist strap, a signal representing a velocity of the chest support with respect to the waist strap, a signal representing an acceleration of the chest support with respect to the waist strap, a signal representing an absolute angle of the chest support, a signal representing an absolute velocity of the chest support, a signal representing an absolute acceleration of the chest support, a signal representing movement of the torque generator, a signal representing a speed of the torque generator, a signal representing acceleration of the torque generator, a signal representing torque of the torque generator, a signal representing a force of the torque generator, a signal representing a wearer's movement, a signal representing a wearer's bending angle, a signal representing a wearer's bending velocity, a signal representing a wearer's bending acceleration, a signal representing a contact force between a wearer and the chest strap, and combinations thereof.

* * * * *